United States Patent
Bishop et al.

(10) Patent No.: US 6,890,903 B2
(45) Date of Patent: May 10, 2005

(54) METHOD FOR INHIBITING THE FORMATION OF SEROMAS USING FACTOR XIII

(75) Inventors: Paul D. Bishop, Fall City, WA (US); Angelika Grossmann, Seattle, WA (US)

(73) Assignee: Zymogenetics Inc., Seattle, WA (US)

( * ) Notice: Subject to any disclaimer, the term of this patent is extended or adjusted under 35 U.S.C. 154(b) by 0 days.

(21) Appl. No.: 10/268,180

(22) Filed: Oct. 9, 2002

(65) Prior Publication Data

US 2003/0087825 A1 May 8, 2003

Related U.S. Application Data

(60) Provisional application No. 60/328,070, filed on Oct. 9, 2001.

(51) Int. Cl.[7] .................. A61K 38/36; C07K 14/745
(52) U.S. Cl. .................. 514/12; 530/380; 530/381; 530/382
(58) Field of Search .................. 514/12; 530/380–382; 424/78.06, 423, 426, 499

(56) References Cited

U.S. PATENT DOCUMENTS

| 5,378,687 A | 1/1995 | Urabe et al. .................. 514/12 |
| 6,197,325 B1 * | 3/2001 | MacPhee et al. ............ 424/426 |
| 6,656,496 B1 * | 12/2003 | Kilpadi et al. .............. 424/448 |

FOREIGN PATENT DOCUMENTS

| EP | 0268772 B1 | 4/1995 |
| EP | 0236978 B1 | 6/1995 |
| EP | 0691850 B1 | 9/2002 |

OTHER PUBLICATIONS

Research Report.
D'Argenio et al., *Dig Dis Sci* 45(5):987–997, 2000.
Nielsen et al., *Cytokines Cell Mol Ther* 3:267–281, 1997.
Bishop et al., *Biochemistry* 29(7):1861–1869, 1990.
Herouy et al., *Lancet* 355:1970–1971, 2000.
Peschen et al., *Vasa* 27(2):89–93, 1998.
Wozniak et al., *Sem Thromb Hemost* 22(5);445–450, 1996.
Mishima et al., *Chirurg* 55:803–808, 1984.
Board et al., *Blood Rev* 7(4):229–242, 1993.
Bregenzer et al., *Z Gastroenterol* 37(10):999–1004, 1999.
Lorenz et al., *Sem Throm Hemost* 22(5):451–455,.1996.
Oshitani et al., *Lancet* 347:119–120, 1996.
Suzuki et al., *Blut* 59(2):162–164, 1989.
Von Bierbrauer et al., *Infusionstherapie und Transfusionmedizin* 24:348–353, 1997.
Utani et al., *J Am Acad Dermatol* 24(3):438–442, 1991.
Kamitsuji et al., *Eur J Pediatr* 146(5):519–523, 1987.
Ichinose et al., *Biochemistry* 25(22):6900–6906, 1986.
Becker et al., *Spinal Cord* 39(2):114–117, 2001.
Isogai et al., *Microsurgery* 11:40–46, 1990.
Weiss et al., *J Cell Physiol* 174:58–65, 1998.
Cario et al., *Scand J Gastroenterol* 485–490, 1999.
Vanscheidt et al., *Acta Derm Venereol (Stockh)* 71:55–57, 1991.

\* cited by examiner

*Primary Examiner*—Robert A. Wax

(57) ABSTRACT

Use of factor XIII for inhibiting the formation of seromas by administering factor XIII. The factor XIII can be administered locally at the site of a wound or surgery or administered systemically. If the factor XIII is administered locally, it can be activated or non-activated and may be administered in conjunction with activated thrombin.

6 Claims, No Drawings

METHOD FOR INHIBITING THE FORMATION OF SEROMAS USING FACTOR XIII

This claims priority under 35 U.S.C. §119(e) of U.S. Provisional Application No. 60/328,070 filed Oct. 9, 2001.

BACKGROUND OF THE INVENTION

Seromas are collections of lymph usually present as painless swellings within a wound or below flaps. These often develop in wounds involving dissection in lymph node-bearing areas, for example axillae, neck, groin etc., or in areas where significant dead space remains such as after abdominal-perineal resection, total mastectomy or in breast reduction procedures either for females or to treat gynecomastia in males. The seromas prevent adequate tissue approximation or may become secondarily infected.

The primary cause lies in the failure to identify and control lymphatic vessels during dissection. Though lymph is a protein-rich fluid, electrocauterization is ineffective to prevent seroma formation. Thus, there is a need to develop a treatment to prevent the formation of seromas.

DESCRIPTION OF THE INVENTION

The present invention fills this need by administering factor XIII to patients who have undergone surgery to inhibit the build-up of fluids or seromas beneath the skin where the surgery took place or a wound has occurred. The factor XIII may be applied locally in solution beneath the skin or administered systemically. The factor XIII solution can be administered prior to surgery, prior to suturing of the surgical site or can be injected beneath the skin after surgery. If the factor XIII is administered locally, it may be activated or non-activated, or the non-activated factor XIII may be applied in conjunction with activated alpha-thrombin. The activated thrombin would then activate the factor XIII. Activated thrombin can be administered locally at a concentration of about 0.5 mg/mL of solution. A method for producing human recombinant thrombin can be found in U.S. Pat. No. 5,502,034.

Factor XIII, also known as fibrin-stabilizing factor, circulates in the plasma at a concentration of 20 µg/ml. The protein exists in plasma as a tetramer comprised of two A subunits and two B subunits. Each subunit has a molecular weight of 83,000 Da, and the complete protein has a molecular weight of approximately 330,000 Da. Factor XIII catalyzes the cross-linkage between the γ-glutamyl and ε-lysyl groups of different fibrin strands. The catalytic activity of factor XIII resides in the A subunits. The B subunits act as carriers for the A subunits in plasma factor XIII. Recombinant factor XIII can be produced according to the process described in European Patent No. 0 268 772 B1. The level of factor XIII in the plasma can be increased by administering a factor XIII concentrate derived from human placenta called FIBROGAMMIN® (Aventis Corp.) or by administration of recombinant factor XIII.

As stated above, administration of factor XIII to a subject is may be administered locally at the site of the wound or systemically. If administered systemically, the factor XIII is generally administered intravenously. When administering therapeutic proteins by injection, the administration may be by continuous infusion or by single or multiple boluses. A pharmaceutical composition comprising factor XIII can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. A suitable pharmaceutical composition of factor XIII will contain 1 mM EDTA, 10 mM glycine, 2% sucrose in water. An alternative formulation will be a factor XIII composition containing 20 mM histidine, 3% wt/volume sucrose, 2 mM glycine and 0.01% wt/vol. polysorbate, pH 8.

Other suitable carriers are well known to those in the art. See, for example, Gennaro (ed.), *Remington's Pharmaceutical Sciences,* 19th Edition (Mack Publishing Company 1995).

Administration of Factor XIII

The levels of factor XIII in an individual can be determined by assays well known in the art such as the BERICHROM®F XIII assay (Dade Behring Marburgh GmbH, Marburg, Germany). The normal adult has an average of about 45 ml of plasma per kg of body weight. Each liter of blood has 1000 units (U) of factor XIII. The amount of factor XIII administered should be enough to bring an individual's level of factor XIII in the plasma to 100% of normal plasma or slightly above to 1–5% above normal. A dose of 0.45 U/kg would raise the level of factor XIII by about 1% compared to normal. One unit of factor XIII is about 10 µg of recombinant factor XIII, which contains only the dimerized A subunit. Thus, to raise the level of factor XIII by 1%, one would administer about 4.5 µg of the A2 subunit per kilogram weight of the individual. So to raise the level 30% of normal, one would administer 13.5 U/kg. For a 75 kg individual this would be about 1,012.5 U. Some patients may have consumptive coagulopathies that involve factor XIII losses. In such cases, a higher dosing (e.g., 1–2 U/kg-%) or multiple dosing of factor XIII (e.g., 1–2 U/kg-%-day) may be required.

EXAMPLE 1

The Use of Factor XIII to Prevent Seroma Formation in a Rat Seromal Mastectomy Model Object of the Experiment The object of the experiment was to determine if factor XIII when given systemically would influence seromal fluid formation using a rat mastectomy model.

Background

Seromas are the most common postoperative complication for patients undergoing a mastectomy. The formation of these fluid collections is facilitated by the disruption of lymphatics and blood vessels as well as by the creation of large potential voids beneath the skin. Postoperative problems due to seroma formation include delayed wound healing, flap necrosis, lymph edema of the arm and infection.

Factor XIII PreparationFactor XIII was provided by ZymoGenetics, Inc., Seattle Wash. in bottles containing 13.2 mg of lyophilized factor XIII containing 0.3 mM ethylenediaminetetraacetic acid (EDTA), 31 mM glycine, and 6.2% sucrose. The lyophilized factor XIII was reconstituted with 3.3 mL of sterile water and pipetted into 0.5 mL aliquots and stored in a freezer at −20° C.

Vehicle Preparation

The vehicle preparation was a lyophilized powder comprised of 0.3 mM EDTA, 31 mM glycine and 6.2% sucrose. This was reconstituted with 3.3 ml of sterile water and pipetted into 0.5 mL aliquots and stored in a freezer at −20° C. After thawing, 0.5 mL of bovine serum albumin (BSA) was added to each vial.

Experimental Procedure

The rats were anesthetized with isoflurane (3% isoflurane, 1% oxygen) and a catheter was inserted into the jugular vein of each rat. Two to three days following catheter insertion, eleven rats received a single intravenous bolus injection through the catheter of the vehicle preparation (the control group) and 12 rats received a single bolus injection of 1 mg/kg of the factor XIII preparation (the experimental group) 30 minutes prior to a left side radical mastectomy. The mastectomy consisted of removal of the pectoralis muscle, lymphatic tissue including nodes (3 or more) and traumatization of subcutaneous lymphovasculature surface. The traumatization the lymphovasculature occurred by scraping 50 times the inner surface of the elevated skin flap with a No. 22 scalpel blade. Five days following mastectomy, the rats were anesthetized with urethane anesthesia. Blood samples were taken for analysis. Seromal fluid was aspirated and weighed from each rat to determine seromal fluid volume and factor XIII content.

Results

No significant differences were observed between the Control and Experimental rats for the following: hematology, clinical blood chemistry and factor XIII levels.

A significant difference was observed in seromal fluid volume aspirate at time of sacrifice (day 5). The control group averaged 2.7 mL of seromal fluid and the group to whom factor XIII was administered averaged 1.4 mL of seromal fluid. Thus factor XIII was effective in inhibiting the formation of seromal fluid.

What is claimed is:

1. A method for inhibiting the formation of a seromal or serous fluid at the site of surgery or a wound in a mammal comprising administring to said mammal a composition comprising an active agent compound that consists of a therapeutically effective amount of factor XIII.

2. The method of claim 1 wherein the factor XIII is administered systemically.

3. The method of claim 1 wherein the factor XIII is administered locally at the site of the surgery wound.

4. The method of claim 3 wherein the factor XIII is activated.

5. A method for inhibiting the formation of seromal or serous fluid at the site of surgery or a wound in a mammal comprising systemically administering to said mammal a therapeutically effective amount of factor XIII.

6. The method of claim 5 wherein the factor XIIII is administered in conjunction with activated thrombin.

* * * * *

UNITED STATES PATENT AND TRADEMARK OFFICE
CERTIFICATE OF CORRECTION

PATENT NO. : 6,890,903 B2 Page 1 of 1
APPLICATION NO. : 10/268180
DATED : May 10, 2005
INVENTOR(S) : Bishop et al.

It is certified that error appears in the above-identified patent and that said Letters Patent is hereby corrected as shown below:

Column 4, line 17, claim 6:
"factor XIIII" should read --factor XIII--.

Signed and Sealed this

Fourth Day of December, 2007

JON W. DUDAS
*Director of the United States Patent and Trademark Office*